(12) United States Patent
Budaraju et al.

(10) Patent No.: US 9,593,348 B2
(45) Date of Patent: Mar. 14, 2017

(54) SYSTEM AND METHOD FOR CONTINUOUS ENZYME ADDITION TO A FERMENTATION PROCESS

(71) Applicant: ROCKWELL AUTOMATION TECHNOLOGIES, INC., Mayfield Heights, OH (US)

(72) Inventors: Srinivas Budaraju, Austin, TX (US); James F. Bartee, Stilesville, IN (US)

(73) Assignee: ROCKWELL AUTOMATION TECHNOLOGIES, INC., Milwaukee, WI (US)

(*) Notice: Subject to any disclaimer, the term of this patent is extended or adjusted under 35 U.S.C. 154(b) by 140 days.

(21) Appl. No.: 14/253,610

(22) Filed: Apr. 15, 2014

(65) Prior Publication Data

US 2015/0291982 A1 Oct. 15, 2015

(51) Int. Cl.
| | |
|---|---|
| C12P 7/06 | (2006.01) |
| C12M 1/34 | (2006.01) |
| C12M 1/00 | (2006.01) |
| C12M 1/40 | (2006.01) |
| C12P 7/14 | (2006.01) |

(52) U.S. Cl.
CPC .............. *C12P 7/06* (2013.01); *C12M 21/12* (2013.01); *C12M 21/18* (2013.01); *C12M 41/46* (2013.01); *C12P 7/14* (2013.01); *Y02E 50/17* (2013.01)

(58) Field of Classification Search
CPC .................................. C12P 7/06; C12M 41/46
See application file for complete search history.

(56) References Cited

U.S. PATENT DOCUMENTS

| | | | |
|---|---|---|---|
| 7,831,318 B2 | 11/2010 | Bartee et al. | |
| 7,933,849 B2 | 4/2011 | Bartee et al. | |
| 8,521,310 B2 | 8/2013 | Axelrud et al. | |
| 8,527,102 B2 | 9/2013 | Noll et al. | |
| 8,571,689 B2 | 10/2013 | Macharia et al. | |
| 8,571,690 B2 | 10/2013 | Bartee et al. | |
| 8,634,940 B2 | 1/2014 | Macharia et al. | |
| 2008/0103747 A1 | 5/2008 | Macharia et al. | |
| 2009/0326695 A1 | 12/2009 | Macharia et al. | |
| 2011/0269114 A1 | 11/2011 | Budaraju et al. | |
| 2011/0312003 A1 | 12/2011 | Budaraju et al. | |
| 2012/0003623 A1 | 1/2012 | Bartee et al. | |
| 2012/0077232 A1 | 3/2012 | Budaraju et al. | |
| 2012/0077244 A1 | 3/2012 | Budaraju et al. | |
| 2013/0183732 A1* | 7/2013 | Mancinelli | C12N 1/14 435/162 |

OTHER PUBLICATIONS

Moon et al., Simultaneous saccharification and continuous fermentation of sludge-containing mash for bioethanol production by *Saccharomyces cerevisiae* CHFY0321. Journal of Biotechnology, vol. 157, No. 4 (Feb. 20, 2012) pp. 584-589.*

* cited by examiner

*Primary Examiner* — Kara Johnson
(74) *Attorney, Agent, or Firm* — Fletcher Yoder P.C.

(57) ABSTRACT

A method for controlling a fermentation process includes injecting a mash into a fermenter and injecting an enzymatic additive into the fermenter on a continuous basis. The enzymatic additive is injected on a continuous basis during at least two time periods: during a batch fill and after the batch fill. The method may be used to control the fermentation processes of one or more fermenters operating in parallel.

12 Claims, 5 Drawing Sheets

SYSTEM AND METHOD FOR CONTINUOUS ENZYME ADDITION TO A FERMENTATION PROCESS

BACKGROUND

The present disclosure relates generally to control systems, and more particularly to process control employing novel techniques for controlling the fermentation process of a biofuel production plant.

A biofuel production plant may include one or more batch processes. One such batch process is the fermentation of a starch source to produce ethanol and other by-products in the presence of yeast and other enzymes in fermenters. A source of nitrogen may also be added to the fermenters to serve as a nutrient for the yeast. A process controller may be used to control certain variables of the fermentation process to achieve specified goals, such as maximizing ethanol production and/or maintaining yeast health. It is now recognized that existing methods of controlling the fermentation process may suffer from disadvantages that may result in decreased ethanol production, inefficient use of yeast, and longer turnaround times for the batch processes.

BRIEF DESCRIPTION

The present disclosure provides, among other things, systems and methods for controlling the fermentation process of a biofuel production plant. In particular, the present techniques are presented in the context of a series of parallel fermenters of the biofuel production plant. More particularly, in various embodiments, the series of parallel fermenters may be coupled to a yeast additive system, a mash additive system, an enzyme additive system, or a combination of these. However, it should be noted that present embodiments may be applied in a wide range of contexts, in a variety of plants, and in any desired industrial, commercial, private, or other setting.

In accordance with one aspect of the present disclosure, a method for controlling a batch fermentation process includes performing a fermenter fill procedure, which includes introducing, separately or together, a mash, yeast, and a first portion of an amylolytic enzyme into a fermenter. The method also includes monitoring a parameter of the batch fermentation process occurring within the fermenter as the yeast ferments glucose released by action of the amylolytic enzyme on the mash to produce ethanol, and introducing a second portion of the amylolytic enzyme into the fermenter based at least partially on the monitored parameter.

In accordance with another aspect, a system for performing batch fermentation processes includes a first fermenter coupled to a yeast source, a mash source, and an amylolytic enzyme source to enable the first fermenter to receive yeast, mash, and an amylolytic enzyme, respectively. The first fermenter is configured to subject the yeast, mash, and the amylolytic enzyme to conditions such that the yeast ferments glucose released by action of the amylolytic enzyme on the mash to produce ethanol. The system also includes an enzyme additive system configured to provide the amylolytic enzyme to the first fermenter from the amylolytic enzyme source, and a control system coupled to the enzyme additive system and configured to direct the enzyme additive system to provide a first portion of the amylolytic enzyme at substantially the same time as the yeast and mash, and to direct the enzyme additive system to provide a second portion of the amylolytic enzyme after all of the yeast and mash are in the first fermenter and as a function of at least one parameter monitored during fermentation.

In accordance with a further aspect, a method for performing batch fermentation processes includes providing mash, yeast, and an amylolytic enzyme into each of a plurality of fermenters. The plurality of fermenters is operationally placed in parallel with respect to one another. The method also includes subjecting the mash, yeast, and the amylolytic enzyme within each fermenter to conditions such that the yeast ferments glucose released by action of the amylolytic enzyme on the mash, continuously introducing, substantially simultaneously into each fermenter during fermentation, a respective additional portion of the amylolytic enzyme. Each additional portion of the amylolytic enzyme is introduced at a respective flow rate that is independent of respective flow rates of the respective additional portions of the amylolytic enzyme introduced into other fermenters.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. The term "consisting of," when used in the context of a mixture of materials, is intended to be defined as limiting the recited components to those specifically recited, except for impurities ordinarily associated with the recited materials. The term "consisting essentially of" is intended to be defined as being limited to the specified materials or steps that do not materially affect the basic and novel approaches described herein. Additionally, it should be understood that references to "one embodiment" or "an embodiment" of the present disclosure are not intended to be interpreted as excluding the existence of additional embodiments that also incorporate the recited features.

Figure 1:
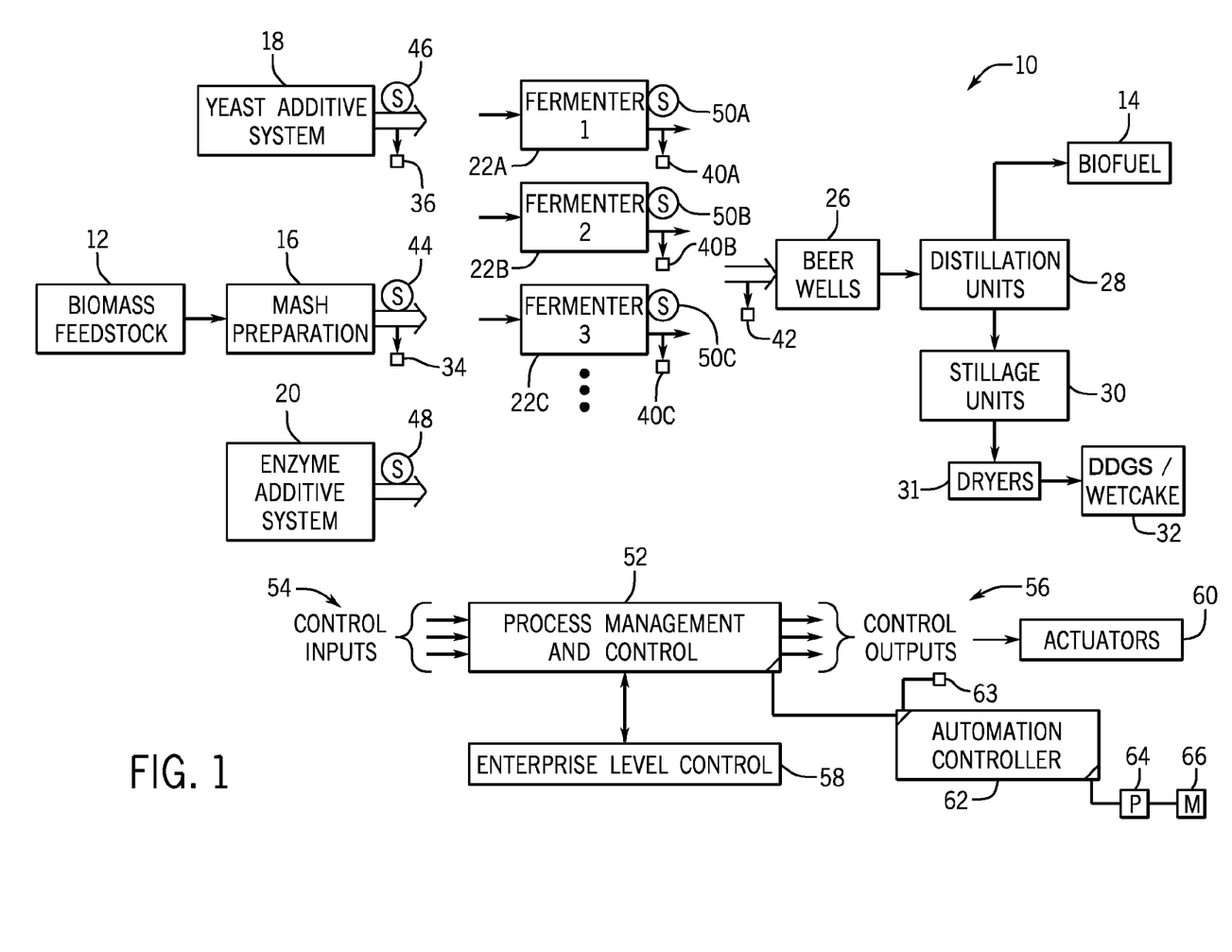
FIG. 1 is a diagrammatical representation of an embodiment of a biofuel production plant having an enzyme additive system configured to continuously add enzymes to fermenters during a fermentation process, in accordance with an aspect of the present disclosure.

FIG. 1 is a diagram of a biofuel production plant 10 illustrating how biomass feedstock 12 may be processed through several stages to produce biofuel 14 in accordance with present embodiments. For example, in one embodiment, the biofuel production plant 10 may be a dry mill ethanol facility that produces ethanol from corn by grinding corn kernels into flour and then forming a slurry or mash by adding water, enzymes, yeast, nutrients, and/or other additives. Although the following discussion pertains to dry mill facilities, certain embodiments may also be applicable to wet mill ethanol facilities that produce ethanol by soaking corn in sulfuric acid and water before grinding. In FIG. 1, one or more of the various stages in the biofuel production plant 10 may be susceptible to various methods of controlling a fermentation process in a closed-loop manner, an open-loop manner, or a combination thereof.

The system 10 may include various systems that enable formation of the mash or slurry on-site. In the system 10 of FIG. 1, a feedstock or biomass 12 (e.g., corn or similar products) is provided to a mash preparation process 16, where water (which may include recycled water) may be added and the biomass 12 may be broken down, for example, to enhance interactions between the biomass 12 and other fermentation reactants by increasing surface area-to-volume ratio. This increase in surface area may allow for sufficient interaction of the water and the biomass 12 to achieve a solution and/or slurry of fermentable materials (e.g., starches, sugars) in water. For example, the starch included in corn may be converted into sugars, such as glucose, using certain types of enzymes. In accordance with embodiments of the present disclosure, this conversion may be carefully controlled to achieve a sugar concentration within a predetermined range. Various approaches for achieving such concentrations are described in further detail below. Cooking (e.g., heating and/or pressurizing) the mixture of biomass 12 and water may promote an increase in the amount of contact between the biomass 12 and water in solution. The separation of carbohydrate biomass from non-carbohydrate biomass may also be increased by cooking.

The output of the mash preparation process 16 (e.g., the fermentation feed or mash) is then sent to one or more fermenters 22, which operate to subject yeast added from a yeast additive system 18, the mash (e.g., source of complex carbohydrates), and one or more enzymes added from an enzyme additive system 20 to fermentation conditions. Three fermenters a first, second, and third fermenter, denoted as 22A, 22B, and 22C respectively, are illustrated. However, any number of fermenters may be present in the system 10. In addition, each of the fermenters 22 may have its own respective feed 24, depicted as 24A for the first fermenter 22A, 24B for the second fermenter 22B, and 24C for the third fermenter. The respective feeds 24 may be totally independent from one another (e.g., each fermenter 22 has its own entire set of feed paths such as sources, conduits, feed control devices), or the respective feeds may be at least partially shared (e.g., the feeds 24 may share a common source but may have entirely separate conduits or feed paths).

In the fermenters 22, yeast, enzymes, and nutrients are used to convert the biomass 12 into a biofuel 14 and by-products, such as carbon dioxide, water, and non-fermentable biomass (solids). Many types of enzymes may be utilized in order to break the complex carbohydrates of the biomass 12 down into smaller oligosaccharides and simple sugars. In some embodiments, the enzymes may be enzymes that perform amylolytic processes (e.g., amylolytic enzymes) on the starch of the biomass 12. The action of the amylolytic enzymes on the complex carbohydrates of the biomass 12 (mash), i.e., the amylolytic process, releases sugars (e.g., glucose, maltose) via breakdown of the carbohydrate linkages that form the starch. These enzymes may be referred to as amylolytic enzymes, amylases (e.g., $\alpha$- and $\beta$-amylases, glucoamylases), and the like. As a specific example, glucoamylase performs amylolytic processes on complex carbohydrates to selectively release glucose (e.g., no other simple sugar is released by action of the glucoamylase on the complex carbohydrates). The simple sugars released by these types of enzymes may be utilized as a nutrient for the yeast, which converts the sugar into, among other things, alcohols (e.g., ethanol), which may be the biofuel 14.

In certain embodiments, the enzymes are stored in an enzyme additive system 20 before injection into the fermenters 22. In some embodiments, the enzyme additive system 20 may store one specific enzyme (e.g., glucoamylase), or one or more enzymes (e.g., glucoamylase and one or more additional amylolytic enzymes). The enzyme additive system 20 of FIG. 1 is also intended to generally encompass various sub-systems and devices that are specifically configured to control the addition of the enzyme (or enzymes) to the fermenters 22. Specific examples of these types of features are described in further detail below with respect to FIG. 4. In a general sense, the enzyme additive system 20 may include various piping (e.g., one or more conduits), flow control devices (e.g., pumps, flow control valves, vent valves), flow meters, other transducers (e.g., pressure, temperature), preparation tanks (e.g., dissolver/suspension tanks), thermal regulation devices (e.g., electric heaters, heat exchangers), and one or more storage tanks to store one or more types of enzymes, among others.

In one aspect of the present disclosure, the enzyme additive system 20 is configured to controllably add the enzyme to the fermenters 22 in a continuous manner. For example, the enzyme additive system 20 may continuously add the enzyme to the fermenters before, during, and after fermenter fill procedures. As discussed in further detail below, the fermenter fill procedures may be complete when all mash (or other source of complex carbohydrates) has been added to the respective fermenter. Thus, even though the example fermentation processes described herein are batch processes (i.e., not continuous), the feed of amylolytic enzyme may be continuous in accordance with embodiments of the present disclosure. The continuous addition of the amylolytic enzyme to the batch fermentation process may enable enhanced control over yeast productivity, thereby increasing efficiency of such processes. Indeed, the control systems and schemes described herein enable the integration of a continuous enzyme addition process with a batchwise fermentation process.

Other feeds may be added to any one or a combination of the fermenters 22. Ammonia, for example, may serve as a nutrient for the yeast (e.g., as a source of nitrogen). The ammonia may be added by an ammonia additive system, or may be added in combination with other feeds. The mash or the yeast, or both, may also include ammonia. In addition, ammonia may be used to control the pH of a fermenter batch. Other sources of nitrogen (e.g., urea), either in addition to or in lieu ammonia may be used.

The yeast additive system 18 may store yeast to be used in the fermenters 22. Examples of yeast types include cream yeast, which is a suspension of live yeast cells in a liquid, siphoned off from growth medium, or dry yeast, or both. Cream yeast may posses several advantages compared to other types of yeast (e.g., block or dry yeast). For example, cream yeast may be transferred immediately from a storage tank to the fermenters 22 whenever the cream yeast is needed during fermentation. On the other hand, the dry yeast may be prepared in a batch process that may last for 7 to 8 hours. Cream yeast may also reduce fermentation variability because cream yeast is not prepared in a propagation tank prior to use. This reduction in variability may enable enhanced control over the fermentation process using kinetic models, predictive models, and the like, which may account for the yeast activity and make certain assumptions or other calculations based on an input relating to the yeast activity. In the discussion that follows, the term "yeast" may be used to refer to cream yeast or any other type of yeast.

Again, the yeast may consume (e.g., ferment) the sugar (e.g., glucose) produced by the action of the amylolytic enzyme (or enzymes) on the complex carbohydrates of the biomass feedstock 12. This fermentation is an exothermic (heat-releasing) process. The generated heat is removed by one or more cooling devices (e.g., heat exchangers such as coolers) in thermal communication with the fermenters 22.

The system 10 may utilize the fermenters 22 in parallel, including more than just the three illustrated (indicated by the vertical ellipsis), to enhance biofuel production. The fermenters 22 may supply beer wells 26, which may be intermediate storage tanks for the products resulting from fermentation. Depending upon the plant design and the number of fermenters, the batch start times may be staggered in order to optimize the utilization of the capacity of the beer wells 26 and smoothly distribute the flow of fermentation feed to the fermentation process and the flow of the biofuel 14 and stillage as output from the fermentation process. In other words, in certain embodiments, the addition of the feeds (e.g., enzymes, yeast, mash) may be staggered in order to achieve a substantially continuous output of the biofuel 14, in order to utilize plant equipment in a more efficient way, or, simply due to plant equipment specifications (e.g., limitations).

By way of example, commercial scale fermenters may take between approximately 8 hours and 16 hours to fill, and may allow the fermentation process to occur for an additional 50 hours to 60 hours before each batch is complete. Accordingly, even a slight reduction in overall fill time or reaction time achieved via enhanced yeast efficiency may ultimately account for a large improvement in the quantities of the biofuel 14 produced by the system 10. In this respect, the present embodiments directed toward the continuous addition of the one or more amylolytic enzymes to the fermenters 22 enable reduced fermenter fill times, and, in certain implementations, reduced batch times achieved as a result of enhanced yeast activity. Thus, the present embodiments may enable improved yield of the biofuel 14 using a substantially unchanged quantity of inputs.

The yield of the fermenters 22, after being temporarily stored in the beer wells 26, may be sent to a distillation process, e.g., one or more distillation units 28, to separate biofuel 14 from water and other liquid constituents, carbon dioxide, and non-fermentable solids. If the biofuel 14 is to be dehydrated to moisture levels less than 5% by volume, the biofuel 14 may be processed through a processing unit that may include molecular sieves, or similar processing equipment (e.g., separators, filters). The finished biofuel 14 may then be processed, such as by denaturing to render it unfit for human consumption.

Water removed by distillation may be used in the form of steam for heat and separation, and condensed water may be recycled back to the mash preparation process 16. Stillage processing units 30 may receive stillage (solids not fermented in the fermenters 22 and yeast residue), the heaviest output of the distillation units 28, for further development of co-products from the biofuel 14 production process. For example, stillage from the stillage processing units 30 may be provided to one or more dryers 31. The dryers 31 may dry at least a portion of the stillage to produce dried distillers grain solids (DDGS) and/or wet cake 32. The DDGS/wet cake 32 may be utilized in other types of fermentation, such as solid state fermentation (SSF), or may be used for another purpose.

A number of sample points may be provided throughout the biofuel production plant 10 where samples may be drawn for analysis. Results of the analysis of the samples may be used in the example control schemes described in further detail below to determine the enzyme rate of addition to each fermenter, among other things. By way of example, a mash preparation sampler 34 may be used to obtain samples to evaluate physical properties and compositional data of the mash (or other complex carbohydrate/hydrocarbon source). A yeast additive system sampler 36 may be used to evaluate the concentration and activity of the yeast. Fermenter samplers 40 (e.g. 40A, 40B, 40C) may, in certain situations, obtain samples at a certain point during fermenter batches to determine concentrations of fermentation products, such as, but not limited to, ethanol, succinic acid, lactic acid, glycerol, acetic acid, and yeast (e.g., to perform a yeast cell count). After the fermenter batch is complete, a fermenter drop sampler 42 may be used to obtain a sample of fermenter product to determine the final concentrations of the same components. Other embodiments of the biofuel production plant 10 may omit some of these samplers or include additional samplers.

In addition to or in lieu of these samples, sensors or similar instrumentation may be placed throughout the plant or system 10 to directly monitor one or more process parameters. In addition, the one or more process parameters may be used as indicators (e.g., feedback) of certain other parameters using conversion factors, modeling, and the like. As an example, sensors may measure process data or operating variables, such as, but not limited to, temperatures, flow rates, pressures, liquid levels, or pH values, in various streams, vessels, or equipment of the biofuel production plant or system 10. Other sensors may be on-line analyzers specifically configured to evaluate feedback indicative of compositional data of streams. In addition to sensors, the operating variables may also be determined using inferential models, laboratory values (as discussed above), or combinations thereof. Information from sensors, models, and so forth may be generally returned to as control inputs when utilized for control in accordance with present embodiments.

By way of specific examples, a mash preparation sensor 44 may be used to measure the flow rate or compositional data of the mash. A yeast additive system sensor 46 may be used to determine the flow rate or activity of the yeast, or to determine baseline values for future evaluations (e.g., a baseline yeast cell count). An enzyme additive system sensor 48 may be used to determine the flow rate of the enzyme, its concentration, and other similar variables. Fermenter sensors 50 (e.g., 50A, 50B, 50C) may be used to determine compositional data, liquid levels, temperatures, pH values, and so forth. It should be noted that each of the illustrated sensors (e.g., 44, 46, 48, 50) may represent multiple sensors that facilitate a single measurement or multiple measurements (e.g., temperature, pressure, composition).

A process management and control system 52 may receive control inputs (e.g., process data) 54 from any one or a combination of the sensors, samplers (e.g., via manual input from a user based on laboratory results, automated input from an on-line analyzer such as a spectrum analyzer and/or chromatograph, or via automated input from a sampling device), or other process-monitoring features of the plant or system 10. Control loops managed by the control system 52 may utilize the control inputs 54 along with set points to generate control outputs 56 to actuators 60 (e.g., valves, pumps, motors) within the plant 10 to control certain aspects of the process being performed by the system 10. For instance, in accordance with present embodiments, the actuators 60 may cause a flow rate of amylolytic enzyme into one or more of the fermenters 22 to be adjusted. Plant operators may be able to monitor the data associated with the control inputs 54 and interact with the control system 52 to provide new set points for various controlled process variables, for example. Based on the data associated with the control inputs 54, input from operators, programming, and/or other inputs, the control system 52 provides the control outputs 56 to the actuators 60 to control various operational parameters of the process (e.g., to control enzyme addition rate to each fermenter 22). In such a configuration, the process management and control system 52 may operate in a closed-loop manner. In the illustrated embodiment, the process management and control system 52 includes an automation controller 62 (e.g., a programmable logic controller (PLC) or application server) and one or more control input and/or output modules 63 (e.g., digital input/output modules, analog input/output modules, specialty modules, power supply modules). The control inputs 54 may be received by such modules 63 and the control outputs 56 may be provided to the actuators 60 via such modules 63. The automation controller 62 includes one or more processors 64 and one or more memories 66 (e.g., hard drives, flash drives, read only memory) that cooperate to provide instructions or logic for control. For example, the automation controller 62 may include one or more sets of instructions that correspond to one or more applications, software packages, or the like, collectively stored on the one or more memories, which are non-transitory, machine-readable media. The one or more sets of instructions stored on the memories 66 are executable by the one or more processors 64 to perform any one or a combination of the processes described herein.

The process management and control system 52 may also be in communication with an enterprise level control module 58, which may be used to manage all information and functions of a business. The enterprise level control module 58 may also be referred to as an enterprise analyzer. Such modules may include computer systems located on-site at the production facility, or off-site, typically coupled to the facility via remote networking components and links. Such enterprise analysis may permit the coordination of production, maintenance, scheduling of delivery of needed materials (e.g., yeast, enzymes, nutrients) and so forth. The process management and control system 52 and the enterprise level control module 58 both generally include, at a minimum, instructions stored collectively on one or more non-transitory memory devices, and processing devices for executing the instructions. The instructions may be grouped together as modules, applications, software, firmware, and so forth. The process management and control system 52 may include, by way of example, automation control systems including controllers, networking devices, servers, workstations, and the like, which may each run distinct sets of instructions to perform at least a portion of the actions described below. In some embodiments, the process management and control system 52 may operate in conjunction with and coordinate the operation of other systems (e.g., legacy distributed control systems).

Figure 2:
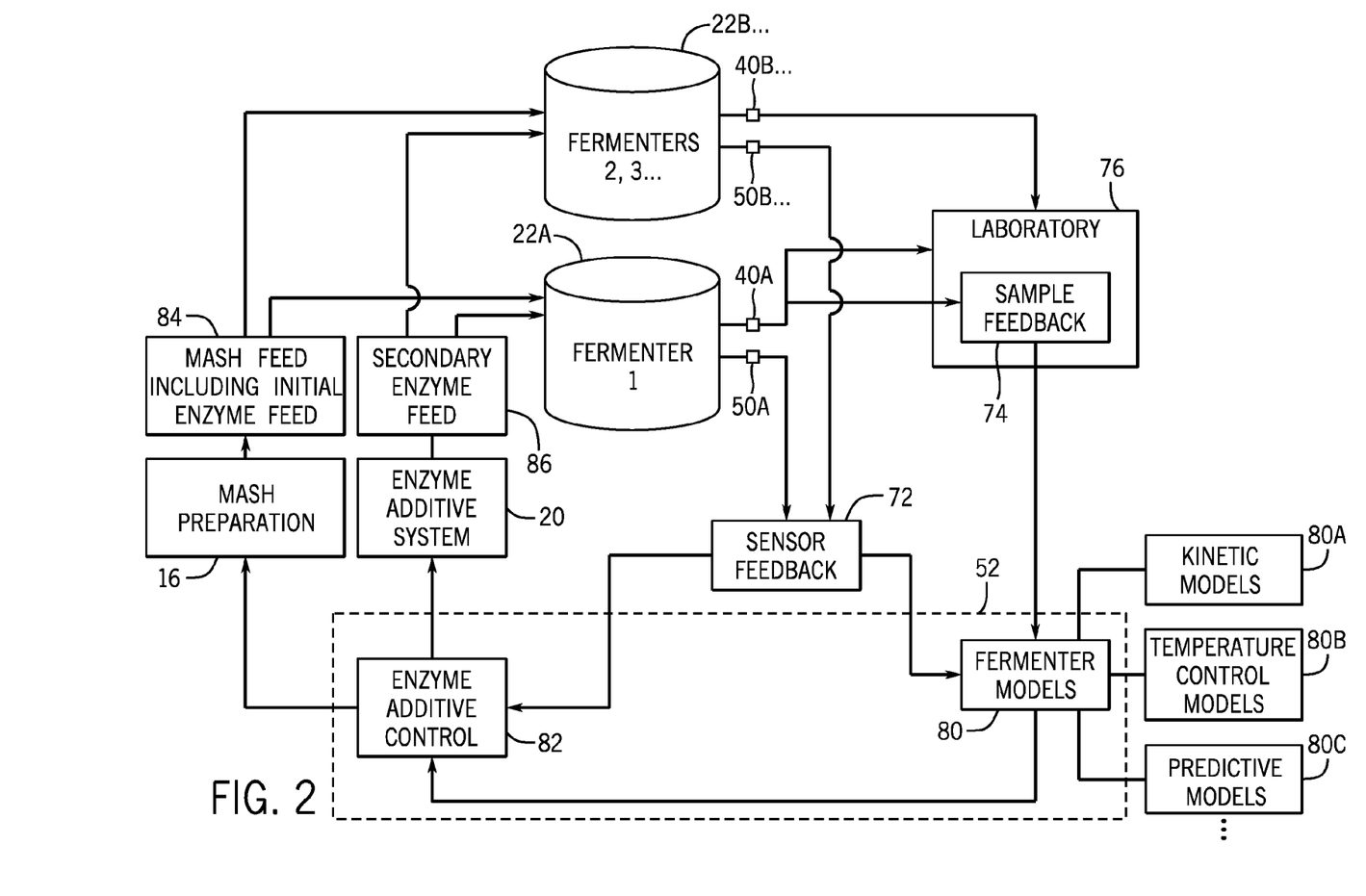
FIG. 2 is a diagrammatical representation of an embodiment of a control system used in the plant of FIG. 1 and configured to control the continuous addition of the enzyme to the fermenters using sensor and modeling inputs, in accordance with an aspect of the present disclosure.

In an aspect of the present disclosure, the process management and control system 52 may control, at least partially, the addition of one or more enzymes to the fermenters 22. An example enzyme addition control scheme 70 is depicted in FIG. 2. The scheme 70 depicts non-limiting examples of various sources of data inputs and outputs occurring during fermentation. For example, during operation (including during startup, fill, and so forth), conditions within the fermenters 22 may change, causing measurable variations in the dynamics of the fermentation process. Generally, as noted above with respect to FIG. 1, the feedback may include sensor feedback 72 generated by directly monitoring physical changes in the fermenters (e.g., temperature, pressure), and sample feedback 74 generated in a laboratory 76 and/or via an automated analyzer from samples taken from the fermenters 22 (or other sources, such as a source of the one or more enzymes, yeast, and/or mash). A variety of standard laboratory methods may be used for the analysis of the samples, including high performance liquid chromatography (HPLC) and pH analysis, which may be commonly available on-site at biofuel production plants (e.g. the system 10). The output from these methods may be raw results, which may include a chromatogram, a list of percent composition of various components, and/or pH values. The raw results may then be subject to further analysis, which may include processing the raw results in the control system 52 to determine additional parameters or reformatting the raw results in a more useful configuration. The resulting sample data 74 may be sent directly to the control system 52. In some embodiments, plant operators may input the results manually.

The process management and control system 52 may use the sensor and/or sample feedback 72, 74 as inputs to one or more fermenter-related models 80, which may be resident in the control system 52 or on systems otherwise linked to the control system 52. By way of example, the fermenter-related models 80 may include kinetic models that model the activity of the yeast based on the real-time feedback and a combination of historical data, historical trends, compositional information relating to the mash, yeast, and enzymes, or any combination thereof. That is, the models 80 may output a modeled (e.g., estimated) yeast activity. Yeast activity may refer to the conversion rate of sugar (e.g., glucose) to ethanol and/or other products (e.g., acids, aldehydes, other alcohols). Additionally or alternatively, yeast productivity, which may refer to the conversion rate per amount of yeast (e.g., amount of ethanol produced per hour per kilogram of yeast), may be a modeled parameter generated based on the sensor and/or sample feedback 72, 74.

The yeast activity and/or productivity may provide an indication as to the efficiency of the fermentation process. That is, if activity and productivity are low, then the fermentation process is likely inefficient. Therefore, it may be desirable for yeast activity and productivity to be maintained at a relatively high level. The yeast activity and productivity may depend on a number of factors, but is, in certain configurations, ultimately rate-limited by the amount of sugar available for fermentation.

The rate-limiting effect of sugar on the yeast activity may apply at both relatively low concentrations of sugar and at relatively high concentrations of sugar in the fermenters 22. For example, if the concentration of sugar is below a determined range, then the amount of sugar being converted into ethanol is not as high as it could be if more sugar were available to the yeast. On the other hand, if the amount of sugar in the fermenter 22 is above a determined range, then the sugar may hinder the activity of the yeast and in some situations, kill the yeast. Indeed, it is presently recognized that production of ethanol or other biofuels on an industrial scale may be deleteriously affected when excess amounts of sugar are present within the fermenters 22. In other words, the sugar may act as negative feedback, hindering the growth of the yeast and associated conversion of sugar to ethanol.

In accordance with the present disclosure, the amylolytic enzyme used to convert complex carbohydrates in the mash to sugar is added continuously through at least a portion of the fermentation process after the fermenters 22 have received all of their mash (e.g., using the mash preparation system 16). In this way, the yeast is provided with a continuously produced amount of sugar that is specifically tailored to achieve a desired yeast activity. Accordingly, the fermenter models 80 may provide one or more inputs, such as a yeast activity (e.g., modeled or estimated) in addition to or in lieu of the sensor feedback 72, to an enzyme additive circuitry or control 82.

The enzyme additive control 82 may be circuitry or a group of instructions, such as a module, stored on non-transitory media of the process management and control system 52, or may be a standalone controller having the instructions stored on non-transitory media with one or more processors for executing the instructions. The enzyme additive control 82 may receive various outputs from the fermenter models 80, such as modeled yeast activity, predicted biofuel production, and the like, to determine an amount of enzyme that should be present within the fermenters 22. In some embodiments, this process may be performed for each fermenter 22 independently, such that the enzyme additive control 82 determines an appropriate amount of enzyme for each fermenter 22. This determination and the addition of the enzyme to multiple fermenters 22 may be performed simultaneously, in certain embodiments. Thus, the addition of enzyme to the fermenters may be independent, but may occur at substantially the same time. The amount of enzyme may correspond, in some embodiments, to a continuous flow rate that is relatively constant, or varies based upon substantially real-time feedback from the sensors and/or fermenter models 80.

The enzyme additive control 82 may output control signals, or similar outputs, for the enzyme additive system 20. The enzyme additive system 20 may then control or otherwise adjust an amount of the enzymes (i.e., one or more enzymes) provided to the fermenters 22, for example by adjusting operating parameters of flow control devices, weighing devices (e.g., if the enzyme is a solid or is supported on a solid, or a paste), conveyors, and the like. As a specific example, the control system 52 (e.g., additive control system 82) may provide an open command to one or more control valves of the enzyme additive system 20, or may provide a start or speed command to a pump (e.g., a secondary enzyme pump) based on an indicated desire for more of a particular enzyme provided by the enzyme additive system 20.

Additionally or alternatively, the enzyme additive control 82 (or the fermenter models 80) may provide signals to the mash preparation system 16, which is used to provide the amylolytic enzymes to the fermenters 22 during the fermenter fill procedures. That is, the system 70 may utilize the mash preparation system 16 to provide the enzymes at a desired initial rate to the fermenters 22 during the fermenter fill procedures. Upon completion of the fermenter fill procedures (i.e., all mash has been added to the fermenters 22), the system 70 may then transition to utilizing the separate, standalone enzyme additive system 20. However, such transitioning is not necessarily required, and the mash preparation system 16 may provide none, some, or all of the enzyme during and/or after the fermentation fill procedure is complete. Conversely, the mash preparation system 16 may not necessarily be utilized to provide any of the enzyme. However, the use of the mash preparation system 16 for providing the initial amount of enzyme during fermenter filling may be desirable to take advantage of any potentially existing equipment that is specifically configured to introduce the enzymes into the mash before the mash is provided to the fermenters 22.

In still further embodiments, the enzyme additive system 20 may be controlled by the enzyme additive control 82 to provide the enzyme to the mash feed being provided to the fermenter via the mash preparation system 16. In this way, at least some of the enzyme feed is provided indirectly to the fermenters 22 by first mixing the enzyme with the mash, and providing the resulting mixture to the fermenters (e.g., during the fermenter fill procedures). Such pre-mixing may be desirable to produce a homogenous mixture of the enzyme and the mash, for instance to avoid potential hot spots in the fermenter 22. Thus, during the fermenter fill procedure, the enzyme may be added to the mash, and the mixture is added to the fermenter. Subsequent to fermenter fill, the enzyme additive system 20 may add the enzyme directly to the fermenters 22.

As an example implementation, a first or initial amount of the enzymes (e.g., glucoamylase) may be added through only a mash header of the mash preparation system 16. For instance, the mash preparation system 16 may add provide a mash feed 84 having the initial feed of the enzyme to the fermenters 22 in an independent manner. Thereafter, the system 70 may utilize the separate, standalone enzyme additive system 20 to introduce a secondary enzyme feed 86. However, it should be noted that the fermenter fill procedures may be completed at different times for the different fermenters 22. Thus, the transition between the initial and secondary feeds of the enzyme may not necessarily occur simultaneously for all of the fermenters 22, but may be staggered relative to one another.

The use of the mash preparation system 16 for providing the initial amount of enzyme during fermenter filling may be desirable to take advantage of any potentially existing equipment that is specifically configured to introduce the enzymes into the mash before the mash is provided to the fermenters 22. Such pre-mixing may be desirable to produce a homogenous mixture of the enzyme and the mash, for instance to avoid potential hot spots in the fermenter 22. Thus, during the fermenter fill procedure, the enzyme may be added to the mash, and the mixture is added to the fermenter. With respect to a single fermenter, subsequent to fermenter fill, the enzyme additive system 20 may add the second feed of the enzyme 86 directly to the fermenter 22.

Further, in certain embodiments, the enzyme additive control 82 may control the mash preparation system 16 and the enzyme additive system 20 at the same time. For example, the control system 52 (e.g., enzyme additive control 82) may perform, using the mash preparation system 16, a fermenter fill procedure in a first one of the fermenters in which an initial portion of the enzyme is added to the first fermenter, while at the same time introducing the second portion of the enzyme 86 to another one of the fermenters using the enzyme additive system 20.

It should be noted that the enzyme additive system 20 may therefore be controlled by the enzyme additive control 82 such that various pumps, valves, and so forth, are controlled to introduce the secondary enzyme feed 86 to a specific fermenter. Indeed, this may be done in an independently controlled manner, at substantially the same time as providing the secondary enzyme feed 86 to other fermenters.

For instance, after completion of a fermenter fill procedure (e.g., all mash has been added to at least one of the fermenters), the system 70 may transition to utilizing the standalone enzyme additive system 20 to add the enzymes (e.g., glucoamylase) to any one or a combination of the fermenters 22 at independent feed rates (including simultaneous addition at independent feed rates).

It should be noted that the block corresponding to fermenter models 80 depicted in FIG. 2 is intended to encompass any number of models used to control any number of parameters of the fermenters 22, additive systems, and so forth. As an example, the fermenter models 80 may include kinetic models 80A that are configured to model the kinetics of the fermentation process based on various inputs into the fermenters 22 (e.g., mash feed amounts, enzyme feed amounts, temperature). As another example, which may be in addition to or in lieu of the kinetic models 80A, the fermenter models 80 may include temperature control models 80B. The temperature control models 80B may be configured to model various processes occurring within the fermenters 22 based on temperature monitoring, and may control various inputs into the fermenters 22 to maintain temperatures of the fermenters 22 to within a certain range.

In addition to or in lieu of the models 80A, 80B, the fermenter models 80 may include one or more predictive models 80C used to predict, for example, biofuel output and/or enzyme activity based on a number of monitored parameters. Further, the fermenter models 80 may be used in various combinations, each model output resulting in possible fermenter adjustments that affect the other models. It should therefore be appreciated that all of the combinations of possible models utilized by the control system 52 are carefully balanced to achieve a desired production rate, temperature, and so forth. Indeed, any number of models may be utilized, as represented by the ellipses. Examples of these types of models (80A, 80B, 80C) are set forth below with respect to FIG. 3.

Figure 3:
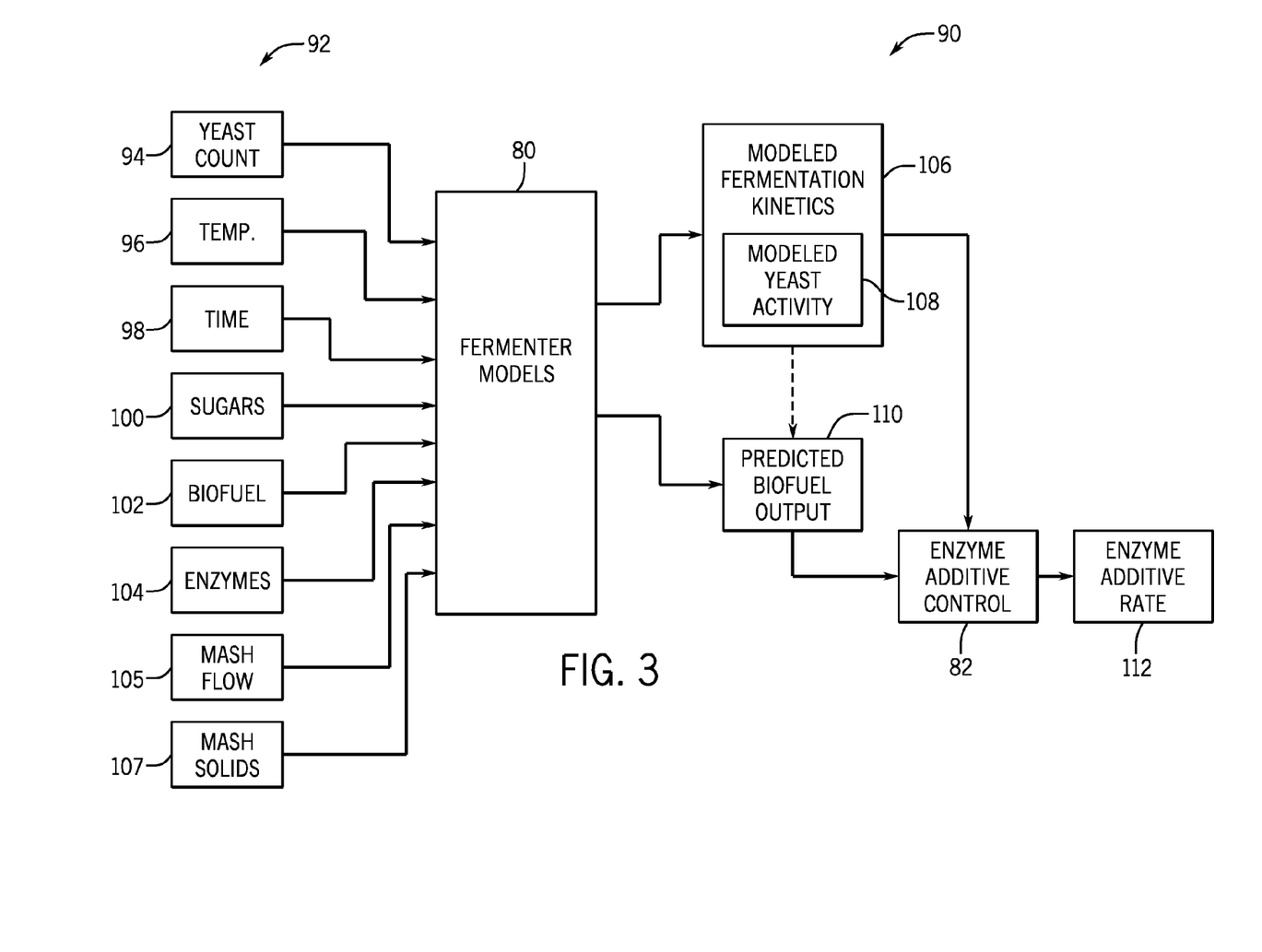
FIG. 3 is a flow diagram depicting an embodiment of the manner in which process feedback is utilized to control continuous enzyme addition to fermenters, in accordance with an aspect of the present disclosure.

An example of the manner in which the one or more fermenter models 80 may operate is depicted in FIG. 3 as a flow diagram 90. The flow diagram 90 is intended to represent, in a general sense, the modeling utilized for each of the fermenters 22 individually. That is, the flow diagram 90 represents certain inputs, outputs, and internal processes that may be associated with the process management and control system 52 as applied to a single fermenter 22. Indeed, because each fermenter 22 is independently controlled and independently receives a particular feed rate of amylolytic enzyme, yeast, and mash, the process management and control system 52 may monitor and control each fermenter 22 independently. However, it should be noted that the fermenter model(s) 80 may utilize feedback from only one of the fermenters 22, a subset of the fermenters 22 (e.g., two or more of the fermenters, but less than all), or all of the fermenters 22, to enhance the accuracy of any modeled (e.g., predicted) outputs.

In the illustrated embodiment, the fermenter models 80 receive various process feedback 92, which may correspond to all or a part of the control inputs 54 of FIG. 1. The illustrated process feedback 92 is intended to be an example only, and is not intended to encompass all possible feedback that the fermenter models 80 may utilize in controlling the addition of the enzyme to the fermenters 22. In FIG. 3, the process feedback 92 includes a yeast count 94, which may be determined in the laboratory 76 either manually (e.g., by a technician) or automatically (e.g., by automated cell counting devices). The yeast count 94 may be pertinent to modeling the yeast activity because the yeast activity directly results in an increase in the number of yeast cells present within the fermenter (i.e., the yeast uses the sugar as fuel to multiply).

The process feedback 92 may further include measured temperature 96, which may also be indicative of fermentation activity. Again, the fermentation is an exothermic process. Accordingly, increases in temperature may be correlative to increases in fermentation (e.g., yeast) activity. This activity may also be indirectly monitored via coolant duty, such as cooling medium flow used to maintain the temperature of the fermenters 22 within a predetermined range.

A time feedback 98 may also be utilized. The time 98 may be used by the fermenter models 80 to ascertain how the various measured and/or modeled parameters of the fermentation process compare to historical values at a particular time during the fermentation process.

Another feedback may include parameters relating to sugar 100 within the fermenter 22. The sugar feedback 100 may be a measure relating to the quantity of sugar within the fermenter 22, the type of simple sugars (e.g., glucose) within the fermenter 22, or both. The sugar feedback 100 may be indicative of the enzyme activity on the complex carbohydrates of the mash, and may, in some embodiments, provide a direct indication as to whether enzyme addition should be increased or decreased. As another example, the amount of sugar present within the fermenter 22 may also be indicative of the quantity of nutrients available to the yeast, and may be used to determine whether the yeast is expected to have a relatively low, relatively high, or average activity relative to historical data.

The process feedback 92 may further include parameters relating to biofuel feedback 102. Examples of such feedback may include the amount of biofuel 14 present within the fermenters 22 (e.g., a biofuel concentration), the composition of the biofuel 14 (e.g., ethanol), a production rate of the biofuel 14, an amount of biofuel 14 relative to other materials in the fermenters 22 (e.g., amount of biofuel 14 relative to fermentation intermediates or by-products), and so on.

Enzyme feedback 104 may also be provided to the fermenter models 80. Examples of such feedback may include enzyme composition (e.g., type and number of different enzymes), enzyme activity (e.g., enzyme catalytic activity to produce simple sugars), enzyme feed concentration (e.g., amount of enzyme provided per unit of enzyme feed), or enzyme feed rate into the fermenters 22, or any combination thereof. In configurations that utilize a liquid enzyme feed, the feed rate may be indicated by a feed pressure, feed flow rate, feed weight, or any combination thereof. The enzyme feed rate may be an indication of a substantially real-time feed rate (e.g., only processing and signal delay between feed measurement and input to the control system), an enzyme feed rate trend (e.g., average feed rate over a period of measurement time, a rate of change of enzyme feed rate over a period of time), or any combination thereof.

The feedback may further include mash flow feedback 105 and mash solids feedback 107. The mash flow feedback 105 may, for example, include a flow rate of the mash along a path extending between the mash preparation 16 (FIG. 1) and the fermenters 22. The mash solids feedback 107 may include, for example, a percentage by weight of solids in the mash, which may be correlated to the amount of hydrocarbon feed present within the mash. When both feedbacks 105, 107 are obtained, the amount of hydrocarbon feed for fermentation being provided to the fermenters 22 may be determined. The rate of addition of hydrocarbon feed, in combination with other feedback relating to addition rates of other fermentation components, may be provided as inputs to model and/or predict certain process parameters, as discussed below.

The fermenter models 80, which may be stored on non-transitory (i.e., non-signal-based) media of the process management and control system 52, and may be executed by processing devices of the process management and control system 52, may utilize any one or a combination of these and other process feedback 92. As an example, the fermenter models 80 (e.g., one or more models that may model one or more aspects of the fermentation process) may utilize a subset of the process feedback 92 at one time during the fermentation process, and may utilize the same subset, a different subset, or all of the process feedback 92 at other times during the fermentation process.

The fermentation models 80 may include, by way of example, a yeast activity model incorporating or utilizing more specific models. For example, the yeast activity model may utilize or may be based on empirical models and/or inferential models, and may also be based on laboratory data, data obtained during fermenter batches, and so forth. One example of such a model is described in U.S. Pat. No. 8,571,690, which is incorporated by reference herein in its entirety for all purposes. The fermenter models 80 may also include or utilize aspects of other models, such as models that utilize target fermenter temperatures and feedback relating to measured fermenter temperature, measured fermenter fill level, and the like, as described in U.S. Pat. No. 7,831,318, which is incorporated by reference herein in its entirety for all purposes.

In one particular embodiment, yeast activity sensors may be utilized to provide estimated yeast activity inputs to bias predicted yeast activity values generated by an inferential dynamic predictive model. This results in an adjustment of the predicted yeast activity, which may be used for control. Such modeling and control is described in U.S. Patent Application Publication No. 2011/0269114, which is incorporated by reference herein in its entirety for all purposes.

The fermenter models 80 may also include or utilize similar modeling as described in U.S. Pat. No. 7,933,849, which is incorporated by reference herein in its entirety for all purposes. In such embodiments, the fermenter models 80 include or utilize a predictive model, which in turn utilizes at least one continuous process model representing at least one continuous process of the biofuel production process, at least one batch process model representing at least one batch process of a biofuel production process, and a continuous simulation framework. In such embodiments, the at least one batch process model interacts with the at least one continuous process model as a nonlinear continuous process via the continuous simulation framework using one or more bridging equations. Control utilizing such a model enables the use of process constraints, process objectives, to generate model outputs. The model outputs may include target values for one or more variables related to the batch fermentation process and the at least one continuous process in accordance with the input objectives, subject to the one or more constraints.

Various other process modeling and control may be implemented at least partially by the fermenter models 80. Other examples of such modeling and control are further described in U.S. Pat. Nos. 8,634,940, 8,571,689, 8,527,102, and 8,521,310, all of which are incorporated by reference herein in their entirety for all purposes. Additional modeling and control is further described in U.S. Patent Application Publication Nos. 2012/0077244, 2012/0077232, 2012/0003623, 2011/0312003, 2009/0326695, and 2008/0103747, all of which are incorporated by reference herein in their entirety for all purposes.

Among other outputs, the fermenter models 80 may generate modeled fermentation kinetics 106, which may include a modeled yeast activity 108. The modeled yeast activity 108 may be a predicted yeast activity. Other modeled fermentation kinetics 106 may include predicted enzyme activity, modeled (e.g., predicted) fermenter temperature, modeled (e.g., predicted) by-product formation, and the like. The fermenter models 80 may also generate a modeled (e.g., predicted) biofuel output 110 by the fermenter 22.

The modeled fermentation kinetics 106 and/or the predicted biofuel output 110, for example, may be provided to the enzyme additive control 82. The enzyme additive control 82 may correspond to a stored set of instructions separate from or integrated with the fermenter models 80. The enzyme additive control 82 may utilize the model outputs to generate an enzyme addition rate 112 to the fermenter 22. The enzyme addition rate 112 may be provided as one or more control signals (e.g., as biasing signals) to adjust one or more process parameters that control or affect the feed of enzyme into the fermenter 22. The feed of the enzyme, in accordance with the present disclosure, is a feed of the enzyme after the fermenter fill procedure is complete. Indeed, in accordance with the present disclosure, the enzyme addition rate 112 is continuously updated during the fermentation process to enable continuous addition of the enzyme (e.g., glucoamylase) to the fermenter 22 after all mash, yeast, and other nutrients are present in the fermenter 22.

Figure 4:
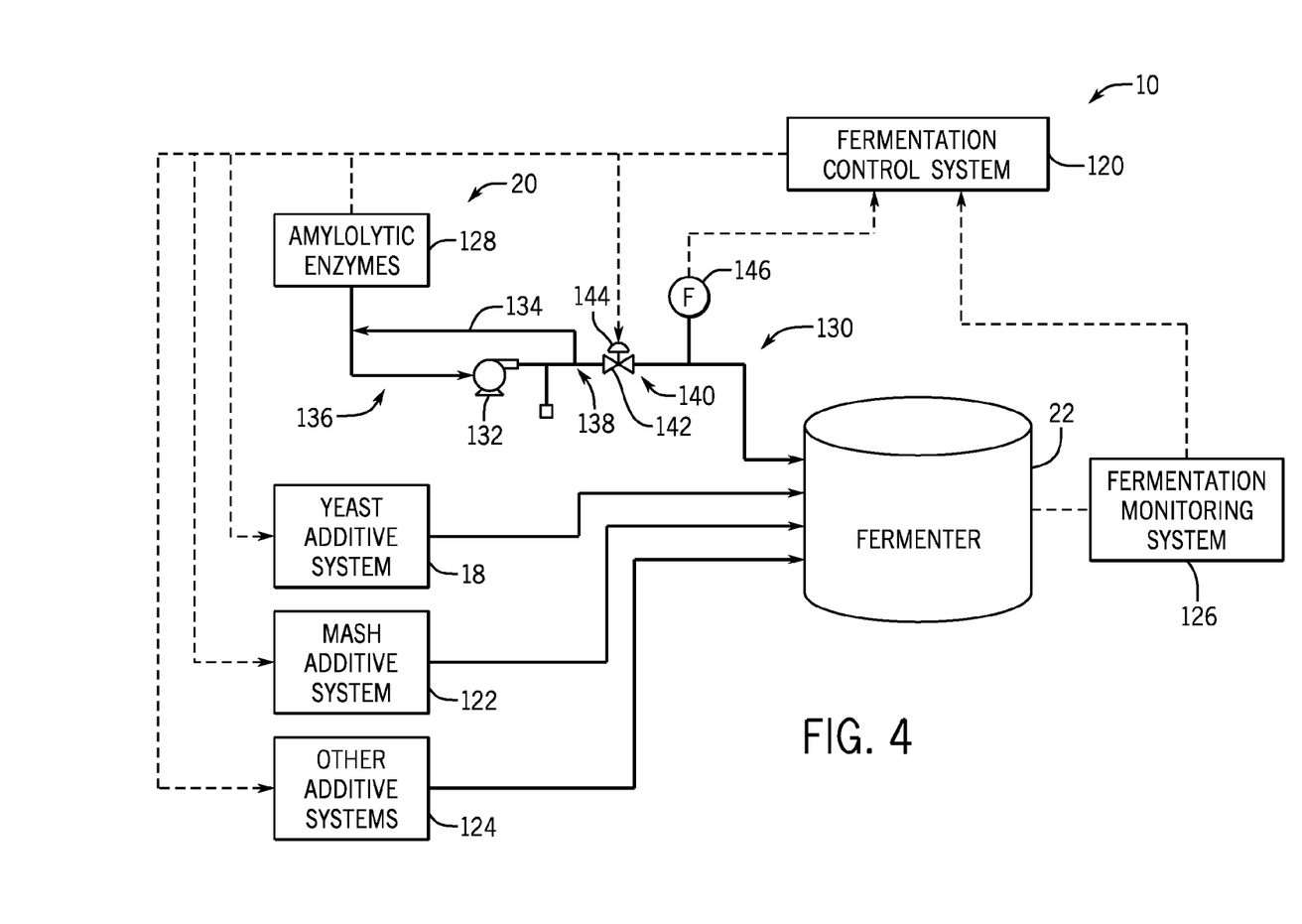
FIG. 4 is a diagrammatical representation of an embodiment of certain functional components of a single fermenter of the biofuel production plant of FIG. 1 configured to continuously provide an enzyme feed to the fermenter, in accordance with an aspect of the present disclosure.

An embodiment of the plant 10 incorporating example enzyme feed control features is illustrated in FIG. 4. The illustrated embodiment of the plant 10 may include all or some of the equipment described above with respect to FIG. 1, and such additional equipment is not shown for clarity. The illustrated plant 10 includes a fermentation control system 120, which may include a standalone system having non-transitory memory and processing devices, or may include a set of instructions (e.g., a module) stored on non-transitory media of the process management and control system 52. The fermentation control system 120 (e.g., implemented as a part of the process management and control system 52) may also generally include various networking equipment to enable communication between the processing devices of the fermentation control system 120 and various control devices, sensors, and instrumentation.

The fermentation control system 120 is illustrated as being communicatively coupled to the yeast additive system 18, a mash additive system 122 (which may be at least a part of the mash preparation system 16), and other additive systems 124. The coupling between the fermentation control system 120 and the additive systems noted above may be communicative in general, and in some embodiments, the coupling between these features may be physical as well. The other additive systems 124 are intended to encompass any one or a combination of other additive systems that may be present, including equipment utilized to provide one or more feeds to the fermenter 22. The fermentation control system 120 may also be communicatively (and in some embodiments, physically) coupled to other effectors of the fermentation process, including cooling systems, heating systems, and downstream equipment for processing the output of the fermenters 22. Indeed, the fermentation control system 120 may cause the additive systems to add feed to one, or more than one of the fermenters at substantially the same time (e.g., simultaneously).

A fermentation monitoring system 126, which may include all or a part of the sensors, instrumentation, laboratory outputs, and so on, used to generate the control inputs (e.g., process data) 54 of FIG. 1, may provide at least some of the control inputs 54 to the fermentation control system 120. However, in other embodiments where the fermentation control system 120 corresponds to a stored module on the process management and control system 52 (which may, itself, be a module and/or other part of the enterprise control system 58), the fermentation control system 120 may not directly receive outputs from the fermentation monitoring system 126, and may only receive outputs from the fermenter models 80. In still further embodiments, the fermentation control system 120 may receive at least one output from the fermentation monitoring system 126, and at least one output from the fermentation models 80.

In the illustrated embodiment, the fermentation control system 120 receives the fermentation model outputs and/or the fermentation monitoring system outputs, and controls the feed of at least one amylolytic enzyme 128 (e.g., glucoamylase) to the fermenter 22 by sending control signals to flow control devices of the enzyme additive system 20. The flow control devices are generally configured to control an amylolytic enzyme feed from a source of the amylolytic enzyme 128 to the fermenter 22 along an enzyme feed path 130. The illustrated enzyme feed path 130 is an example, and is not particularly limited to a single conduit, or the illustrated flow control devices. Indeed, any number of conduits and flow control devices suitable for performing the acts described herein may be used. Furthermore, the illustrated embodiment depicts only one fermenter 22 for clarity, and is not intended to limit the scope of its associated description to the use of a single fermenter. Rather, as noted above, the present embodiments enable feed of enzymes, mash, yeast, and other fermentation materials to the fermenters in an independent but simultaneous fashion.

The illustrated flow control devices include an enzyme pump 132 (which may represent one or more pumps) that motivates the enzyme 128 along the enzyme feed path 130 toward the fermenter 22. The enzyme pump 132 may be of any suitable type and construction appropriate for pumping the enzyme feed. In certain embodiments, the enzyme pump 132 may be a continuous output pump that provides a relatively constant pressure increase across its inlet and outlet. In such embodiments, the path 130 may include a recycle flow 134 to avoid over-pressurization of the path 130 and to enable other flow control devices to throttle the enzyme feed.

In other embodiments, the pump 132 may be a variable displacement or similar pump that is communicatively coupled to the fermentation control system 120. In such embodiments, the enzyme pump 132 may be used as at least one flow control device (e.g., as one of a combination of components) to vary the feed rate of the enzyme into the fermenter 22. That is, the fermentation control system 120 employs control signals to the enzyme pump 132 (and one or more additional flow control devices such as more than one pump, more than one valve, and so forth) to vary its displacement to change enzyme addition rate. However, as described herein, it should be borne in mind that the enzyme addition rate is at least periodic after all mash has been added to the fermenter 22 (e.g., after the fermenter fill procedure), and is in some embodiments, continuous. Thus, after fermentation fill procedures have been completed for a plurality of fermenters (e.g., independently but substantially simultaneously), enzyme addition rate into the plurality of fermenters may also be independent but simultaneous and, in certain embodiments, continuous.

The enzyme pump 132 may be disposed along a first portion 136 of the path 130, upstream of a point 138 where the recycle flow 134 diverges from the feed path 130, as well as one or more flow control valves 140. The one or more flow control valves 140 may include a valve portion 142 placed along a conduit of the path 130, and an actuator 144 that controls the valve portion 142. The fermentation control system 120 may send control signals to the actuator 144 to adjust the valve portion (e.g., its position) to adjust enzyme flow along the path 130. The fermentation control system 120 may also send control signals to other actuators and other effectors (e.g., pumps) to control the overall enzyme flow along the path 130.

A flow meter 146 or similar device positioned downstream of the one or more flow control valves 140 provides feedback to the fermentation control system 120 relating to the enzyme feed rate to the fermenter 22. In embodiments where multiple flow meters are present along the feed path 130, any number of flow meters may be positioned downstream thereof in order to ensure that all flow control valves are functioning properly.

In still further embodiments, the pump 132 may be a variable displacement pump and may be used in combination with the one or more flow control valves 140 to control and adjust the enzyme feed rate into the fermenter 22. The fermentation control system 120 may control the pump 132 and flow control valves 140, in some configurations, to enable operational headroom between a maximum flow operation and a current operational position. For example, rather than use the variable displacement pump at full output to achieve a relatively high feed rate, the fermentation control system 120 may direct the enzyme pump 132 to operate at less than full displacement and direct the one or more flow control valves 140 to operate at a position corresponding to relatively high flow. In this way, the fermentation control system 120 may use the pump 132 (when variable displacement or the like) to make large (e.g., coarse) enzyme feed rate adjustments, and may use the flow control valves 140 to make smaller (e.g., fine) enzyme feed rate adjustments. Such operation may be particularly desirable in accordance with embodiments of the present disclosure, which may utilize a continuous enzyme feed to the fermenters 22, rather than a batch feed of the enzyme to the fermenters 22 that is completed at the end of the fermenter fill process.

It should be noted that the illustrated embodiment of FIG. 4 is intended to apply to all fermenters 22 of the plant 10, or only one of the fermenters 22, or only a subset of fermenters 22. Indeed, the plant 10 may include multiple independent enzyme feed paths coupling the enzyme source 28 to each fermenter (i.e., each fermenter has its own feed path for the enzyme). In such configurations, the fermentation control system 120 may individually control the feed rates along the respective enzyme feed paths of the fermenters 22 using independently-controlled flow control devices (e.g., pumps, flow control valves). In doing so, the production of each fermenter 22 is separately controlled to achieve a desired output of the biofuel 14, and the time taken to complete the fermenter fill process for each fermenter 22 may be reduced.

Figure 5:
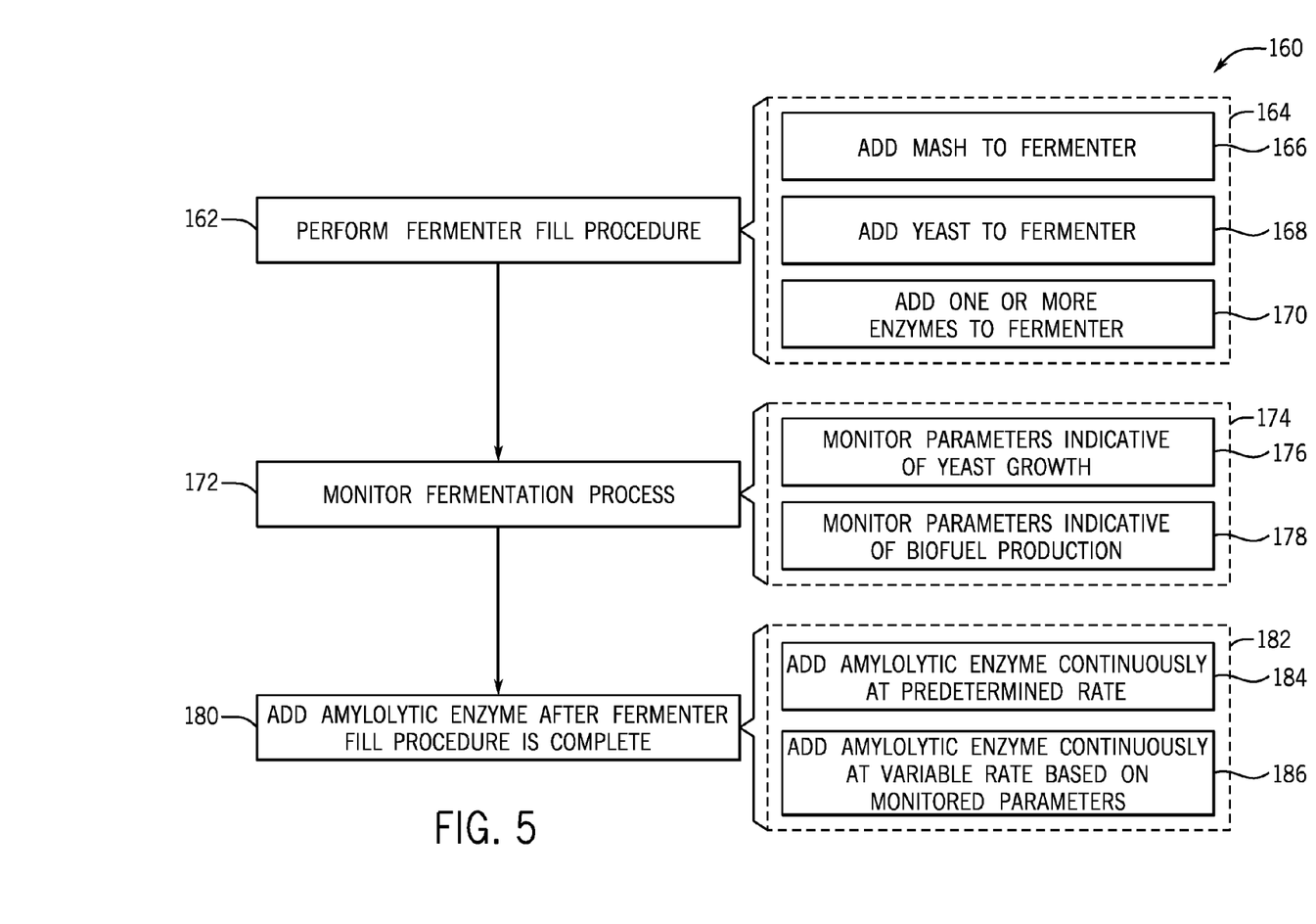
FIG. 5 is a flowchart of an embodiment of a method for controlling a fermentation process, including continuously providing an enzyme feed to a fermenter after a fermenter fill procedure, in accordance with an aspect of the present disclosure.

With the foregoing in mind, FIG. 5 provides an example method of operating the plant 10 to produce the biofuel 14 via continuous enzyme (e.g., glucoamylase) addition to the fermenters 22. FIG. 5, in particular, is a process flow diagram illustrating a method 160 of controlling continuous enzyme addition to a single fermenter 22. However, the method 160 may be applied independently to multiple fermenters 22 present within the plant 10, even in embodiments where certain resources (e.g., sources of materials) are shared.

In FIG. 5, the method 160 includes performing (block 162) a fermenter fill procedure. The fermenter fill procedure in accordance with block 162 may include a number of sub-processes 164, a few of which are illustrated as examples in FIG. 5. The sub-processes 164 may include adding (block 166) mash to the fermenter 22, for example via one or more mash feed paths and using one or more mash flow control devices. The mash, again, may be a source of complex carbohydrates in the fermenter 22. The mash feed rate to the fermenter 22 may be substantially continuous during the fermenter fill process, and no further mash is typically added thereafter.

The sub-processes 164 may also include adding (block 168) yeast to the fermenter 22. The acts represented by block 168 may include adding cream yeast and/or propagated yeast into the fermenter 22 via one or more yeast feed paths, which may be shared or entirely separate from the mash feed paths. The yeast feed rate to the fermenter 22 may be substantially continuous during the fermenter fill process, and no further yeast is typically added thereafter.

The fermenter fill procedure will also generally include adding (block 170) one or more of the amylolytic enzymes to the fermenter 22. In accordance with present embodiments, less than the entire quantity of enzyme used during the overall batch fermentation procedure is added during the fermenter fill procedure. This amount may be referred to herein as a "first portion" of the enzyme added to the fermenter 22 during the fermenter fill procedure. The fermenter fill procedure, as noted above, may be considered to be complete once all of the mash, yeast, or a combination thereof, has been added to the fermenter 22. The first portion of the enzyme added to the fermenter 22 may be determined, for example, by the fermenter models 80, as well as feedback relating to the amount and/or composition of the yeast and mash. In certain embodiments, the first portion of the enzyme may be an amount to sustain and encourage yeast growth/activity during a first stage of the fermentation process. Indeed, as noted above, it has been found that subjecting the yeast to excessive amounts of simple sugar produced by the action of the enzymes on the mash may hinder yeast activity.

Upon initiation of fermentation, the method 160 may include monitoring (block 172) the fermentation process. The acts represented by block 172 may include monitoring any one or a combination of parameters indicative of any one or a combination of the process feedback 92 described above with respect to FIG. 3. In a general sense, one example objective of monitoring in accordance with block 172 is determining whether the addition of amylolytic enzyme to the fermenter 22 will encourage or discourage yeast activity during fermentation, as well as what range of enzyme feed (e.g., flow rate, amount) will likely be suitable to encourage enhanced yeast activity.

The acts represented by block 172 may include one or more monitoring sub-processes 174, such as sub-processes 174 that provide indications relating to one or more fermentation processes that may not be directly measured. Indeed, the monitoring sub-processes 174 may provide outputs that are used as inputs to any one or a combination of the models described above. The sub-processes 174, in the illustrated embodiment, generally include monitoring (block 176) one or more parameters indicative of or otherwise relating to yeast growth. Similarly, the sub-processes 174 may also include monitoring (block 178) one or more parameters indicative of biofuel production. The acts represented by blocks 176 and 178 may include monitoring temperature changes in the fermenter 22 (e.g., indicative of an exothermic process such as glycolysis to change glucose into pyruvate), pressure changes in the fermenter 22 (e.g., indicative of $CO_2$ release resulting from glycolysis), yeast counts (e.g., directly relating to yeast cell reproduction), and so on.

In accordance with the present approach, the method 160 includes adding (block 180) an amylolytic enzyme (e.g., glucoamylase) to the fermenter 22 in a continuous manner after the fermenter fill procedure is completed. Typically, the fermenter fill procedure completion is characterized by a stoppage in the addition of mash and/or yeast to the fermenter 22, as noted above. However, there may be other indicators, such as a halt in nutrient feed, initiation of fermentation via application of heat, control of fermentation via thermal regulation of the fermenter 22, and the like. Indeed, any other indicators that the fermentation process is underway and under active control by the process management and control 52, and the enzyme is added in a continuous manner thereafter, is presently contemplated.

Again, one example objective of adding the amylolytic enzyme to the fermenter 22 in a continuous manner throughout the fermentation process is to regulate yeast activity by regulating the production of simple sugars used as a growth nutrient by the yeast. When added in a continuous manner, the amount of amylolytic enzyme added to the fermenter 22 may be represented as a feed rate, as described above. The feed rate may or may not be regulated during performance of the method 160, as represented by feed sub-processes 182.

The feed sub-processes 182 in FIG. 5 include adding (block 184) the amylolytic enzyme continuously at a predetermined rate. The acts represented by block 184 may be performed for the entire fermentation process, or for only a portion of the fermentation process. For instance, the method 160 may include continuously adding the amylolytic enzyme (e.g., glucoamylase) to the fermenter 22 at a predetermined rate for a predetermined amount of time, and thereafter possibly adjusting the rate as a result of re-evaluating the enzyme feed rate based on modeled and/or monitored process variables.

The sub-processes 182 may, in addition to or in lieu of the acts represented by block 184, include adding (block 186) the amylolytic enzyme continuously to the fermenter 22 at a variable rate based on one or more monitored (and/or modeled) parameters. In this way, the method 160 includes varying the feed rate of the enzyme (e.g., glucoamylase) to the fermenter 22 to account for certain process variables, target parameters (e.g., target yeast activity, target biofuel production rate, target yeast growth rate), available resources (e.g., available pump power and/or available flow adjustment), and so on. In some embodiments, the continuous addition of the enzyme at the variable rate may be performed throughout the entire fermentation process, i.e., the entire process of fermenter fill and throughout fermentation until fermentation is completed (e.g., no appreciable/useful quantity of fermentable hydrocarbons remain).

It is also contemplated that the sub-processes 182 (which may also include other variations of the addition of enzyme to the fermenter 22, such as "shots" of enzyme added by injection into the fermenter 22) may be performed in any order, in any combination. As one example, the sub-processes 182 may include continuously adding the enzyme to the fermenter 22 at a predetermined rate for a predetermined time, followed by (or preceded by) continuously adding the enzyme to the fermenter at a variable rate in response to process variables (e.g., modeled and/or monitored fermentation parameters).

Again, the continuous addition of the enzyme (e.g., glucoamylase) may enable an increase in the stability of yeast growth by mitigating the presence of excessive amounts of simple sugars that would otherwise discourage yeast growth. There may be other benefits to this continuous addition, as well as other problems addressed thereby. However, it should be noted that in a large-scale implementation involving extensive control and automation for biofuel production, the integration of continuously adding enzymes to the fermenter as described herein can greatly enhance fermenter efficiency, reduce fill and fermentation times (which can typically take days) by, for example, 20% or more, and overall, enable more cost-effective production of the biofuel 14.

While only certain features of present embodiments have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for controlling a batch fermentation process, comprising:
performing a fermenter fill procedure comprising introducing, separately or together, a mash, yeast, and a first portion of an amylolytic enzyme into a fermenter, wherein the fermenter fill procedure is complete when all mash and yeast to be used in the batch fermentation process has been injected into the fermenter;
monitoring a parameter of the batch fermentation process occurring within the fermenter after the fermenter fill procedure is complete and as the yeast ferments sugar released by action of the amylolytic enzyme on the mash to produce ethanol; and
introducing a second portion of the amylolytic enzyme into the fermenter after the fermenter fill procedure is complete and in response to monitoring of the parameter performed after the fermenter fill procedure is complete.

2. The method of claim 1, wherein introducing the second portion of the amylolytic enzyme into the fermenter comprises introducing the second portion of the amylolytic enzyme at different time points after the fermenter fill procedure is complete.

3. The method of claim 1, wherein introducing the second portion of the amylolytic enzyme into the fermenter comprises continuously introducing the second portion of the amylolytic enzyme for at least a time period occurring after the fermenter fill procedure is complete.

4. The method of claim 1, wherein, during the fermenter fill procedure, the first portion of the amylolytic enzyme is continuously introduced into the fermenter as a function of flow rate of the mash, the yeast, or a combination thereof, flowing into the fermenter.

5. The method of claim 1, wherein the monitored parameter comprises a temperature of components in the fermenter, a concentration of the sugars, a concentration of complex carbohydrates in the mash, a measurement of solids in the fermenter, a yeast cell count from an aliquot taken from the fermenter, or any combination thereof.

6. The method of claim 1, wherein the monitored parameter comprises a predicted ethanol production, wherein the predicted ethanol production is generated using a measured physical parameter of components in the fermenter as an input to a kinetic model that outputs the predicted ethanol production.

7. The method of claim 1, wherein the monitored parameter comprises a modeled yeast activity derived from a yeast activity model.

8. The method of claim 1, wherein the amylolytic enzyme is glucoamylase.

9. The method of claim 1, wherein introducing the second portion of the amylolytic enzyme into the fermenter comprises introducing the second portion of the amylolytic enzyme into the fermenter with a first pump and substantially simultaneously introducing a third portion of the amylolytic enzyme into an additional fermenter with a second pump.

10. The method of claim 9, wherein the third portion of the amylolytic enzyme introduced into the additional fermenter is based at least partially on a monitored parameter of components within the additional fermenter.

11. The method of claim 1, comprising:
performing the fermenter fill procedure for each of a plurality of fermenters; and
continuously introducing, substantially simultaneously into each fermenter during fermentation and after each respective fermenter fill procedure, a respective second portion of the amylolytic enzyme, wherein each second portion of the amylolytic enzyme is introduced at a respective flow rate that is independent of respective flow rates of the respective second portion of the amylolytic enzyme introduced into other fermenters.

12. The method of claim 1, wherein the fermenter fill procedure, the monitoring of the parameter of the batch fermentation process, and the introduction of the second portion of the amylolytic enzyme are at least partially performed by a control system comprising non-transitory media storing instructions and a processor configured to execute the stored instructions, wherein the control system is configured to direct an enzyme additive system to provide the first portion of the amylolytic enzyme at substantially the same time as the yeast and mash, and to direct the enzyme additive system to provide the second portion of the amylolytic enzyme after the fermenter fill procedure is complete.

* * * * *